US00PP14081P3

(12) United States Plant Patent
Zipperer, III

(10) Patent No.: US PP14,081 P3
(45) Date of Patent: Aug. 19, 2003

(54) GLADIOLUS PLANT NAMED 'PRISSY'S PURPLE'

(76) Inventor: John O. Zipperer, III, 13590 Brynwood Ln., Ft. Myers, FL (US) 33912

( * ) Notice: Subject to any disclaimer, the term of this patent is extended or adjusted under 35 U.S.C. 154(b) by 0 days.

(21) Appl. No.: 09/918,662

(22) Filed: Jul. 31, 2001

(65) Prior Publication Data

US 2003/0028943 P1 Feb. 6, 2003

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed Dec. 20, 2000.
U.S. patent application Ser. No. 09/742,726, Zipperer, III, filed Dec. 20, 2000.
U.S. patent application Ser. No. 09/877,571, Zipperer, III, filed Jun. 8, 2001.
U.S. patent application Ser. No. 09/877,572, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/877,575, Zipperer, III, filed Jun. 8, 2001.
U.S. patent application Ser. No. 09/918,660, Zipperer, III, filed Jul. 31, 2001.
U.S. patent application Ser. No. 09/918,663, Zipperer, III, filed Jul. 31, 2001.

*Primary Examiner*—Bruce R. Campell
*Assistant Examiner*—Anne Marie Grünberg
(74) *Attorney, Agent, or Firm*—Hahn Loeser & Parks LLP; Laura G. Barrow

(57) ABSTRACT

A new and distinct gladiolus variety, designated 'Prissy's Purple', is shown and described. The variety is characterized by having a heavy stem that is about 128 cm in length and containing 20–22 florets when grown from Jumbo size corms in Ecuador. One arrangement of the variety consists of six petals, namely three large petals, two medium petals, and one small petal. In another arrangement, the bloom consists of two large petals, three medium petals, and one small petal. The corolla bloom is characterized by having purple specks (Purple Group N78A) deep within the throat. The color of the bloom tight is Red Purple Group 72B, and the color of the bloom in open perfect condition is Purple Group N78C.

2 Drawing Sheets

The present invention comprises a new and distinct variety of a *Gladiolus l.*referred to by the variety name 'Prissy's Purple.'

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed (the Applicant's selected provisional breeder's designation is 26-2). The female parent was a rich purple gladiolus variety named 'Spartan,' an unpatented released variety characterized in part by having heavy, but not particularly tall stems (i.e. 110–115 cm from Jumbo size bulbs) and week resistance to Fusarium species. The male parent was a lavender gladiolus variety named 'T-704', a released unpatented variety characterized by having a short stem with a long head for a total stem length of 110–155 cm. The seeds were planted in Ft. Myers, Fla., and the selection of the 'Prissy's Purple' variety was made in Spring 1988. Asexual reproduction of the 'Prissy's Purple' variety was achieved by collecting cormels from the first corm and growing said cormels to maturity in Ft. Myers. All subsequent asexual reproductions of the 'Prissy's Purple' variety remain true to the original variety type.

BOTANICAL DESCRIPTION

Figure 1:
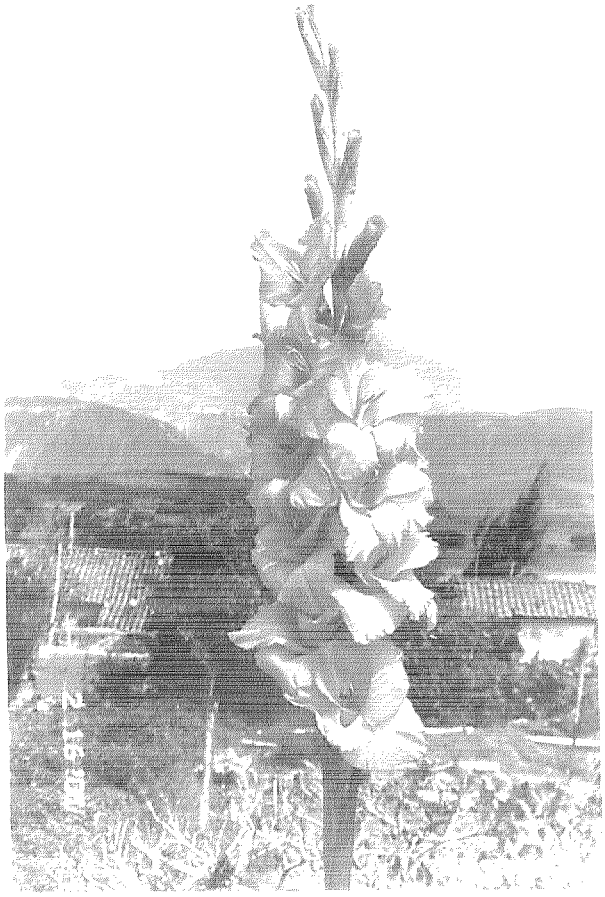
FIG. 1 is a photograph of a 'Prissy's Purple' variety plant in bloom.
Figure 2:
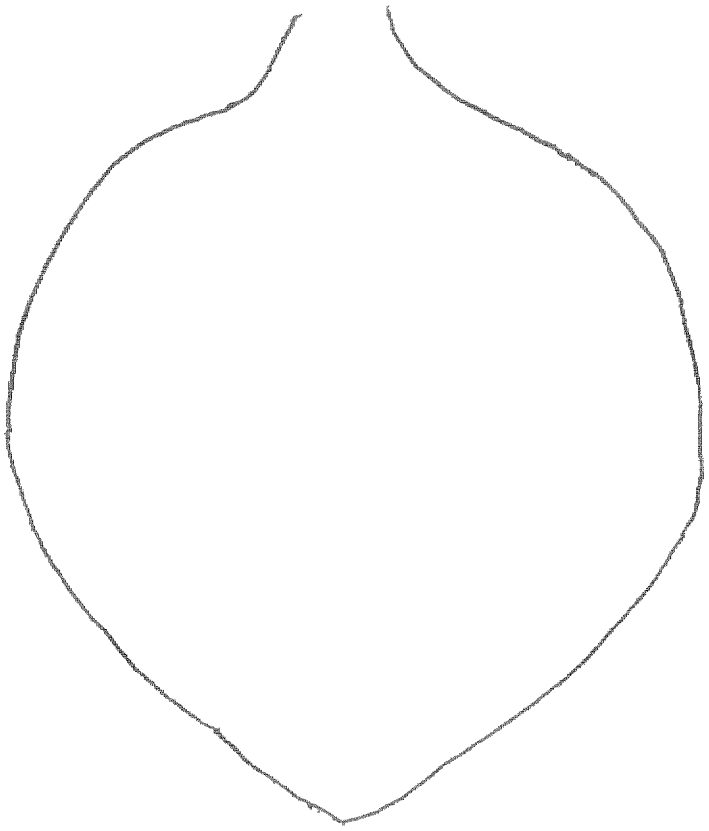
FIG. 2 is a drawing illustrating the shape and size of the large petals.

The accompanying color photograph (FIG. 1) shows the inflorescence and various stages of blooming of the 'Prissy's Purple' variety plant.

The following botanical description, except for color, of the 'Prissy's Purple' variety was observed when the plant was 95 days old grown under the following conditions in Ecuador:

1) Twelve-hour daylight days with high light intensity;

2) Temperatures: 58–60° F. (low's) and 69–75° F. (high's);

3) Humidity: 50–55%

4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 128 cm and contains 20–22 florets when grown from Jumbo size corms (1.75 inch and larger) in Ecuador. The stem diameter is 1.4 cm just below the lower floret (in Florida). The color of the stem is Yellow Green Group 144C. The head length is about 68 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes). The leaf color of the 'Prissy's Purple' variety is Green Group 137C. The leaf size is about 80 cm (length) by 4.8 cm (width).

The bud size of the 'Prissy's Purple' variety is about 6.5 cm in length with a bloom diameter of 12 cm. The color of the bloom tight is Red Purple Group 72B. The color of the bloom open perfect condition is Purple Group N78C. The color of the bloom open going down is Purple Group N78D. The corolla bloom has purple specks (Purple Group N78A) deep within the throat. The inner part of the small petal as well as the line that bisects the outer portion of the small petal are White Group N155B. The color of the outer part of the petal is Purple Group N78C.

In one arrangement, the flowers of the variety each consist of a total of six petals, namely three large petals, two medium-size petals, and one small petal. Generally, the large petals are oriented on the top half of the flower, the two medium flowers are oriented on the lower half of the flower (about 4:00 and 8:00), and the small flower is positioned between the two medium petals (about 6:00). Alternatively, the variety may have two large petals located in the top half of the flower, three medium petals, and one small petal on the lower half of the flower near the bottom of the bloom.

The variety has three stamens and one pistil. The color of the pistil (all parts) is White Group 155B. The color of the stamen head is Purple Group 79C and White Group 155B on the backside of the head. The color of the stamen stem is Yellow Green Group 144B, with the top of the stamen stem having a Red Purple Group 64B color.

The corms of the 'Prissy's Purple' variety are typical for the gladiolus and have a Yellow Group 8B color under the husk on the top of the bulb one day after harvest.

GENERAL OBSERVATIONS

The 'Prissy's Purple' variety, like the parent 'Spartan,' is a slow variety in that it takes 94 to 96 days to harvest when grown in Ecuador. 'Prissy's Purple' differs from the 'Spartan' variety, however, in that it has a much higher number of florets per stem (i.e. four to six more florets). The 'Prissy's Purple' variety also has a greater ability to produce florets in mid-winter compared to the 'Spartan' variety. Both the 'Spartan' and 'Prissy's Purple' varieties have heavy stems; however, 'Spartan' has a very short stem compared to 'Prissy's Purple.'

'Prissy's Purple' is most similar to the male parent 'T-704' variety in that it has a long flower head, a high floret count per stem, and a stem that is slightly shorter than normal compared to average commercial gladiolus varieties. The very long head length of the 'Prissy's Purple' variety does make up for this stem shortness, however, in that the overall length of the 'Prissy's Purple' variety is longer than both of its parents by 10 to 15 cm.

The variety usually produces one to two stems per Jumbo size corm. The variety can maintain up to nine flowers in open bloom simultaneously in a vase of water and should be harvested with a minimum of three florets showing color in order to open well. The variety is an excellent opener after transport, in that the stems may be cut tight, shipped dry for a week, and still bloom well afterwards. The first bloom of the 'Prissy's Purple' variety takes three days to open after the stem is placed in water and lasts three days thereafter. The stem finishes blooming in eleven days.

The 'Prissy's Purple' variety has good resistance to fungi diseases and is much more resistant to attack by Fusarium fungi than the 'Spartan' variety, but has similar resistance to Fusarium compared to 'T-704'. 'Prissy's Purple' has a much better resistance to Botyris and Curvalaria species than the parent 'T-704', however.

The variety does not emit a fragrance.

I claim:

1. A new and distinct gladiolus variety of plant, 'Prissy's Purple', as shown and described herein.

* * * * *